(12) United States Patent
Kaplan et al.

(10) Patent No.: US 12,576,045 B2
(45) Date of Patent: *\*Mar. 17, 2026*

(54) METHODS AND NUTRACEUTICAL COMPOSITIONS FOR THE PREVENTION AND/OR MITIGATION OF VEISALGIA

(71) Applicant: Kaplan IP, LLC, Hallandale Beach, FL (US)

(72) Inventors: Linda J. Kaplan, Hallandale Beach, FL (US); Rachel S. Kaplan, Hallandale Beach, FL (US)

(73) Assignee: Kaplan IP, LLC, Hallandale Beach, FL (US)

( * ) Notice: Subject to any disclaimer, the term of this patent is extended or adjusted under 35 U.S.C. 154(b) by 503 days.

This patent is subject to a terminal disclaimer.

(21) Appl. No.: 18/164,913

(22) Filed: Feb. 6, 2023

(65) Prior Publication Data

US 2023/0181488 A1 Jun. 15, 2023

Related U.S. Application Data

(60) Continuation-in-part of application No. 17/374,116, filed on Jul. 13, 2021, now Pat. No. 11,571,395, (Continued)

(51) Int. Cl.
*A61K 31/366* (2006.01)
*A61K 9/00* (2006.01)
(Continued)

(52) U.S. Cl.
CPC ............ *A61K 31/05* (2013.01); *A61K 9/0014* (2013.01); *A61K 9/0053* (2013.01); (Continued)

(58) Field of Classification Search
CPC .... A61K 31/05; A61K 9/0014; A61K 9/0053; A61K 31/145; A61K 31/197;
(Continued)

(56) References Cited

U.S. PATENT DOCUMENTS

| | | | |
|---|---|---|---|
| 6,399,114 | B2 | 6/2002 | Foreman |
| 2010/0273895 | A1 | 10/2010 | Stinchcomb et al. |
| 2015/0342923 | A1 | 12/2015 | Powell |

FOREIGN PATENT DOCUMENTS

WO 0071145 A1 11/2000

OTHER PUBLICATIONS

Kaplowitz, The Yale Journal of Biology and Medicine, 54 (1981),497-502 (Year: 1981).*

* cited by examiner

*Primary Examiner* — San Ming R Hui
(74) *Attorney, Agent, or Firm* — Maier & Maier, PLLC

(57) ABSTRACT

Nutraceutical compositions and the methods for preventing and/or mitigating veisalgia by the administration thereof. The nutraceutical compositions address the challenged state of the individual and potentiate their ability to be compliant with treatment when the metabolic functions of the liver are overwhelmed as alcohol metabolism depletes hepatic supplies of needed molecules. The methods provide the nutraceutical composition directly to the end organs where alcohol and toxin infused blood is also metabolized and neutralized.

14 Claims, 4 Drawing Sheets

Related U.S. Application Data which is a division of application No. 16/408,994, filed on May 10, 2019, now Pat. No. 11,096,904.

(60) Provisional application No. 62/670,265, filed on May 11, 2018.

(51) Int. Cl.

| | |
|---|---|
| *A61K 31/05* | (2006.01) |
| *A61K 31/145* | (2006.01) |
| *A61K 31/197* | (2006.01) |
| *A61K 31/341* | (2006.01) |
| *A61K 31/355* | (2006.01) |
| *A61K 31/4415* | (2006.01) |
| *A61K 31/455* | (2006.01) |
| *A61K 31/51* | (2006.01) |
| *A61K 31/525* | (2006.01) |
| *A61K 31/714* | (2006.01) |
| *A61K 33/00* | (2006.01) |
| *A61K 33/30* | (2006.01) |
| *A61P 43/00* | (2006.01) |

(52) U.S. Cl.

CPC .......... *A61K 31/145* (2013.01); *A61K 31/197* (2013.01); *A61K 31/341* (2013.01); *A61K 31/355* (2013.01); *A61K 31/366* (2013.01); *A61K 31/4415* (2013.01); *A61K 31/455* (2013.01); *A61K 31/51* (2013.01); *A61K 31/525* (2013.01); *A61K 31/714* (2013.01); *A61K 33/00* (2013.01); *A61K 33/30* (2013.01); *A61P 43/00* (2018.01)

(58) Field of Classification Search

CPC ................ A61K 31/341; A61K 31/355; A61K 31/4415; A61K 31/51; A61K 31/525; A61K 31/714

See application file for complete search history.

METHODS AND NUTRACEUTICAL COMPOSITIONS FOR THE PREVENTION AND/OR MITIGATION OF VEISALGIA

CLAIM OF PRIORITY

This application is a continuation-in-part application of U.S. application Ser. No. 17/374,116, filed on Jul. 13, 2021, which is a divisional application of U.S. application Ser. No. 16/408,994, filed on May 10, 2019, now U.S. Pat. No. 11,096,904, which claims priority from U.S. Provisional Patent Application No. 62/670,265, filed on May 11, 2018, the entire contents of each are hereby incorporated by reference.

BACKGROUND

Consumption of alcohol has an attendant morbidity known as veisalgia. Symptoms of veisalgia are related to the adverse impact upon organs including but not limited to the brain, muscles, kidney, skin, gastrointestine, heart, liver, etc. with attendant symptoms that include but are not limited to: fatigue, thirst, drowsiness, headache, dry mouth, slurred speech, dysphagia, nausea, vomiting, weakness, poor concentration, poor coordination, dysbasia, confusion, memory loss, reduced alertness, brain fog, anxiety, impaired judgment, depression, loss of appetite, body ache, malaise, myalgia, polyuria, diuresis, irritability, photophobia, gastritis, bloating, facial flush including but not limited to Rosacea flush and Asian flush, neck and face diaphoresis, rapid heartbeat, stupor, loss of consciousness, and ultimately coma and/or death.

As long as humans have been imbibing fermented beverages, they have sought remedies (aka the prior art) for the expectant experience of veisalgia. The prior art targets ingestion for its delivery system, but ingestion is self-defeating, in the state of veisalgia.

An attendant of veisalgia is nausea, and the thought of and/or the act of ingesting a handful of dry capsules or a big slug of nasty-tasting liquid often invokes dysphagia, thus limiting an individual's compliance with the dosage regimen of an ingestion-targeted delivery system, and, ultimately, the system's efficacy.

Prior art efforts to mask the bad taste of ingestibles increases caloric content, which also adversely impacts an individual's compliance with dosage regimen of an ingestion-targeted delivery system and its efficacy, for those challenged with sugar metabolism including but not limited to Diabetes, Obesity and or Metabolic Syndrome. With presenting veisalgia symptoms of anxiety, loss of appetite and nausea, prior art has exceedingly limited opportunity for proper and meaningful ingestion, absorption and/or effectiveness.

Referencing compliance with an ingestion-targeted delivery system that requires a large liquid dose, the TSA restricts the transport of liquids. It is well established that one drink on a plane in flight is equivalent to 3 drinks on the ground due to altitude, oxygenation and pressurization. Thus, compliance with a large liquid dosage regimen for an ingestion-targeted treatment system is impeded during a flight.

All prior art has significant drawbacks including but not limited to efficacy, delivery and compliance with the dosage regimen.

Moreover, the prior art has failed to consider adequately preventing or mitigating veisalgia by effectively administering comprehensive nutraceuticals to provide support to molecules in the liver and at the end organs.

The inventors recognized that there is a need to resolve the problems associated with the prior art's delivery systems, solubility, palatability and potency for preventing and mitigating veisalgia.

Those skilled in the art could not have recognized that a composition such as the invention could be tenable, effective, pleasant or possible.

SUMMARY

Accordingly, it is an object of the invention to provide novel methods and a novel nutraceutical composition to ameliorate veisalgia including but not limited to prevention and mitigation. Certain exemplary embodiments of the invention address the challenged metabolic functions of the liver, which are overwhelmed as alcohol metabolism depletes hepatic supplies of needed molecules, by providing the nutraceuticals that support the molecules in the liver. Certain exemplary embodiments of the invention provide nutraceuticals elsewhere in the body to the end organs where alcohol and toxin infused blood is also metabolized and neutralized.

By providing support to molecules in the liver and at the end organs, with the utilization of alternative delivery systems, the invention is uniquely effective with much lower concentrations and dosages of actives that support the molecules both for prevention and mitigation.

BRIEF DESCRIPTION OF THE FIGURES

Advantages of embodiments of the invention will be apparent from the following detailed description of the exemplary embodiments. The following detailed description should be considered in conjunction with the accompanying figures in which:

FIG. 2 also demonstrates how nutraceutical enriched blood becomes oxygenated (ONE) and outlines distribution of ONE throughout the body. FIG. 2 demonstrates both ONE distribution directly to the brain via arterial branches of the internal and external carotid arteries passing approximate to and through the mouth as well as venous distribution to the lungs where oxygenation occurs thus providing ONE to all end organs including but not limited to the liver and brain as ONE passes through the aorta and into the arterial vasculature supply.

DETAILED DESCRIPTION

Aspects of the invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
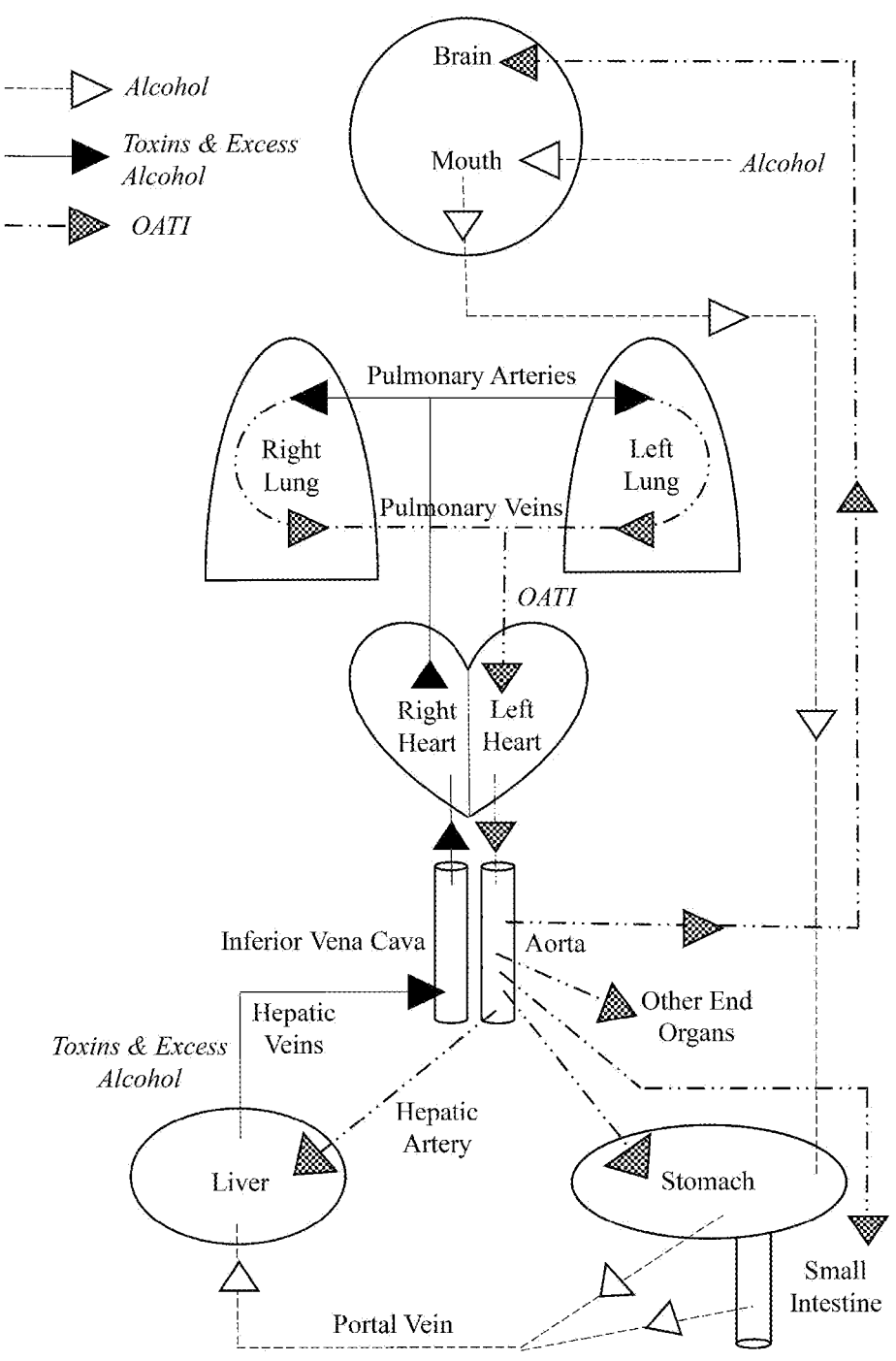
FIG. 1 illustrates alcohol absorption, toxin circulation, and Oxygenated alcohol and toxin-infused blood (OATI) circulation to the end organs of the body.

During alcohol intake and absorption, alcohol is transported from the lumens of the stomach and small intestine (or gastrointestine) into their venous collection system. The gastrointestinal venous collection system coalesces with other veins to form the portal vein. The portal vein carries deoxygenated alcohol infused venous blood from the gastrointestinal tract to the liver where it is neutralized via metabolism. The alcohol absorption and toxin circulation is illustrated in FIG. 1.

The rate of metabolism of alcohol by the liver is impacted by hepatocyte stores of molecules, enzymes, coenzymes and availability of nutrients including but not limited to: alcohol dehydrogenase (ADH), aldehyde dehydrogenase (ALDH), cytochrome P450 (including but not limited to CYP2E1), catalase, glutathione, nicotinamide adenine dinucleotide phosphate (NADPH) and nicotinamide adenine dinucleotide

4 pulmonary veins to the left heart. From the left heart, OATI is transported via the aorta to end organs, such as the brain, nose, mouth, skin, digestive tract, liver, pancreas, lungs, kidneys, and other parts of the body through their arterial branches from the aorta. Veisalgia occurs as the end organs are exposed to OATI. This can be understood from FIG. 1.

The invention addresses the challenged metabolic functions of the liver, which are overwhelmed as alcohol metabolism depletes hepatic supplies of needed molecules, by providing the nutraceuticals that support the molecules in the liver. The invention may also provide nutraceuticals elsewhere in the body to the end organs where alcohol and toxin infused blood is also metabolized and neutralized. As OATI incites damage and inflammation to the end organs, the endocannabinoid system additionally participates in repair notably in the gastrointestine and brain. By providing support to molecules in the liver and at the end organs, along with alternative delivery systems, the invention is uniquely effective with much lower concentrations and dosages of actives that support the molecules both for prevention and treatment, including prevention and mitigation.

The invention relates to methods of administering to an individual 30 minutes prior to alcohol consumption, during alcohol consumption, after alcohol consumption, or the day following alcohol consumption, a therapeutically effective amount of a nutraceutical composition to prevent or mitigate veisalgia, which may include, but is not limited to, prevention, mitigation and/or relief of veisalgia.

The nutraceutical composition includes flavonoids, antioxidants, vitamins, minerals, amino acids, electrolytes and/or anti-inflammatory and metabolic support agents as the active nutraceuticals some of which are referenced in Table 1.

TABLE 1

| | Antioxidant | Supports Brain Function | Liver Detoxifier | Supports Liver Function | Supports Basic metabolism | Immune Booster | Anti-Inflammatory | Enzyme Building Blocks | Prevents/blocks Cell Injury | Repairs Damaged Cells | Electrolyte | Anti-Stress | Support Cellular Energy |
|---|---|---|---|---|---|---|---|---|---|---|---|---|---|
| Vitamin B1 | | X | | | X | | | X | | | | | |
| Vitamin B2 | X | | | | X | | | | | | | | X |
| Vitamin B3 | | X | X | | X | | | X | X | | | | X |
| Vitamin B5 | | X | X | | X | | | | | | | | X |
| Vitamin B6 | X | X | X | | X | | | | | | | | X |
| Vitamin B9 | X | X | | X | X | | | X | | X | | | |
| Vitamin B12 | X | X | | X | X | | | X | | X | | X | X |
| Potassium Citrate | | X | | | X | | | | | | X | | |
| Vitamin C | X | | | | | X | X | | | | | | |
| Vitamin E | X | | | | | X | X | | X | | | | |
| Zinc Citrate | | X | X | | X | X | X | X | | | | | X |
| L-Glutathione | X | X | X | X | X | X | X | | X | X | | X | X |
| Dihydromyricetin (DHM) | | X | X | | | | X | | | X | | | |
| Silymarin (Milk Thistle) | X | | X | | | X | X | | X | X | | | |
| Taurine | X | X | X | | | | X | | | | | X | |

(NAD+), hereinafter referred to collectively as molecules. These molecules are located within cell structures including but not limited to: cytosol, microsomes, peroxisomes, endoplasmic reticulum, and mitochondria.

When ingestion and absorption of alcohol exceeds and exhausts the liver's capacity to metabolize the load, deoxygenated alcohol and toxin-infused blood drains to the inferior vena cava which empties into the right heart. The right heart sends this blood to the lungs via the pulmonary arteries. In the lungs the blood is oxygenated. Oxygenated alcohol and toxin-infused blood (OATI) is carried by the Exemplary nutraceuticals suitable for the composition include acetyl L carnitine, adenine, *aloe vera*, Alpha lipoic acid, *Angustifolia*, Asian pear, basil, Vitamin B7, black currant, *boswellia*, bromelain, black pepper, *calcium*, cannabinoids including but not limited to cannabidiol (CBD), chia seed, choline, *chromium*, cinnamon, clove, copper, *Cucumis melo*, curcumin, dihydromyricetin, *eclipta alba, flax* seed, Vitamin B9, ginger, glutathione, inositol, iron, *kiwi, kava kava*, lavender, nutmeg, magnesium, manganese, matcha, Vitamin B12, silymarin, N-acetyl cysteine, L-Glutathione, Vitamin B3, olive, omega 3 fatty acid, oregano, Vitamin B10, Vitamin B5, papain, papaya, pineapple, potassium, prickly pear, Vitamin B6, quercitrin, Vitamin B2, rosemary, saffron, selenium, shisandra, taurine, Vitamin B1, tulsi, turmeric, ubiquinone, Vitamin C, Vitamin E, yakriton, and zinc. The particular combination of nutraceuticals depends upon the biological function or mechanism of interest, such as providing support to molecules in the liver, brain, immune system, gastrointestine, skin, pancreas, kidney, neutralizing OATI, or supporting replenishment of glucose and energy. Of course, a combination of nutraceuticals may be selected to address more than one biological function or mechanism of interest by the administration of a single composition.

The amount or concentration of the nutraceuticals in the composition varies, for example, based on the biological functions or mechanisms of interest, dosage form, particle size of the nutraceuticals, the dosing regimen and the delivery route.

The nutraceutical composition may include pharmaceutically acceptable excipients and carriers suitable for facilitating administration of the nutraceutical composition and/or controlling the release of the nutraceuticals. For example, pharmaceutically acceptable excipients and carriers include but are not limited to water, alcohol, glycerin, sorbitol, microcrystalline cellulose, crospovidone, stearic acid, magnesium stearate, citric acid, silicon dioxide, liposomes, microspheres, nanoparticles, nanowater, transferosomes, ethosomes, lipid based systems, quercetin, genistein, naringin, sinomenine, piperine, gallic acid, glycyrrhizin and nitrile glycoside for delivery of nutraceuticals as chewables, tablets, fast melt tablets, quick dissolving tablets, capsules, caplets, gel caps, liquids, sprays including but not limited to atomizers, vaporizers, aerosol or pump sprays, droplets, auto-injectors, suppositories, or enemas. Additionally, liposomes, microspheres, microemulsions, nanoparticles, nanoemulsions, nanowater, transferosomes, polymeric micelle, ethosomes, lipid based systems, bile salts, surfactants, fatty acids, chelating agents, ethylene glycol, tetraacetic acid, ethylene diamine tetraacetic acid, salicylates, polymers, chitosan, quercetin, genistein, naringin, sinomenine, piperine, glycyrrhizin, nitrile glycoside, *Cuminum cyminum* Linn., luteolin, *Zingiber officinale*, lysergol, allicin, *aloe vera, Alternanthera sessilis L., Artemesia arborescens*, rutin, zedoary, triptolide, *cuscuta chinensis*, lignans, artemisinin, capsaicin, colchicines, vincristine, gingko biloba, silybin, ginseng, ginsenoside, matrine, ammonium glycyrrhizinate, sodium laurel sulfate, silk fibroin, glycerol tristearate, monostearin, trikatu, humectants, emollients, exfoliants and surfactants may be selected that are suitable for delivery of the nutraceuticals by creams, lotions, solutions, ointments, patches, gels, strips, films, powders, liquids, fast absorbing tablets, quick dissolving tablets, sprays including but not limited to atomizers, vaporizers, aerosol or pump sprays, droplets, and or auto-injectors, hereinafter referred to as administration of the nutraceuticals. The nutraceutical compositions may also include natural flavors, flavoring agents, fragrances, sweeteners and sucralose depending on the methods of administration.

In some exemplary embodiments, nutraceuticals are micronized and/or nanonized hereinafter referred to as Methods. Typically, the teeth, tongue, salivary glands and stomach participate in digestion, the process of making consumables into smaller units for absorption in the gastrointestine. Milling and grinding nutraceutical compositions into the smallest possible sizes and shapes is for the purpose of potentiating absorption. Through micronization and nanonization the particulate size of the nutraceuticals potentiates absorption directly into the vascular system. This results in streamlined delivery of nutraceuticals with immediate onset of beneficial activity and ability to target organs directly. Bypassing the digestive system has many benefits as the use and efficacy is not impacted by states that can limit the use and efficacy of an ingestable including but not limited to dysphagia, malaise, nausea, vomiting, bloat and gastritis. Micronization is a process wherein solid particulate matter is milled or ground using modern techniques such as the Hammer, Conical, Ball or Roller mill systems to reduce the size of a particle to the micrometer range of 1 micron (0.001 millimeter) or less. In this embodiment the micronization range is from 0.1 microns to 250 microns and nanonization ranges from to 0.01 nm to 10 nm. Flame Spray Pyrolysis (FSP) generates nanoparticles of 0.01 to 0.1 nm. Solid Lipid Nanoparticles (SLN) and Nanostructure Lipid carriers are in the range of 1 to 500 nm. These Methods improve bioavailability and efficacy of a particle. These Methods enhance the transport of nutraceuticals particles between cell junctions (intercellular diffusion) and across cell membranes (intracellular diffusion). The smaller the particle size, the better the transport.

Figure 2:
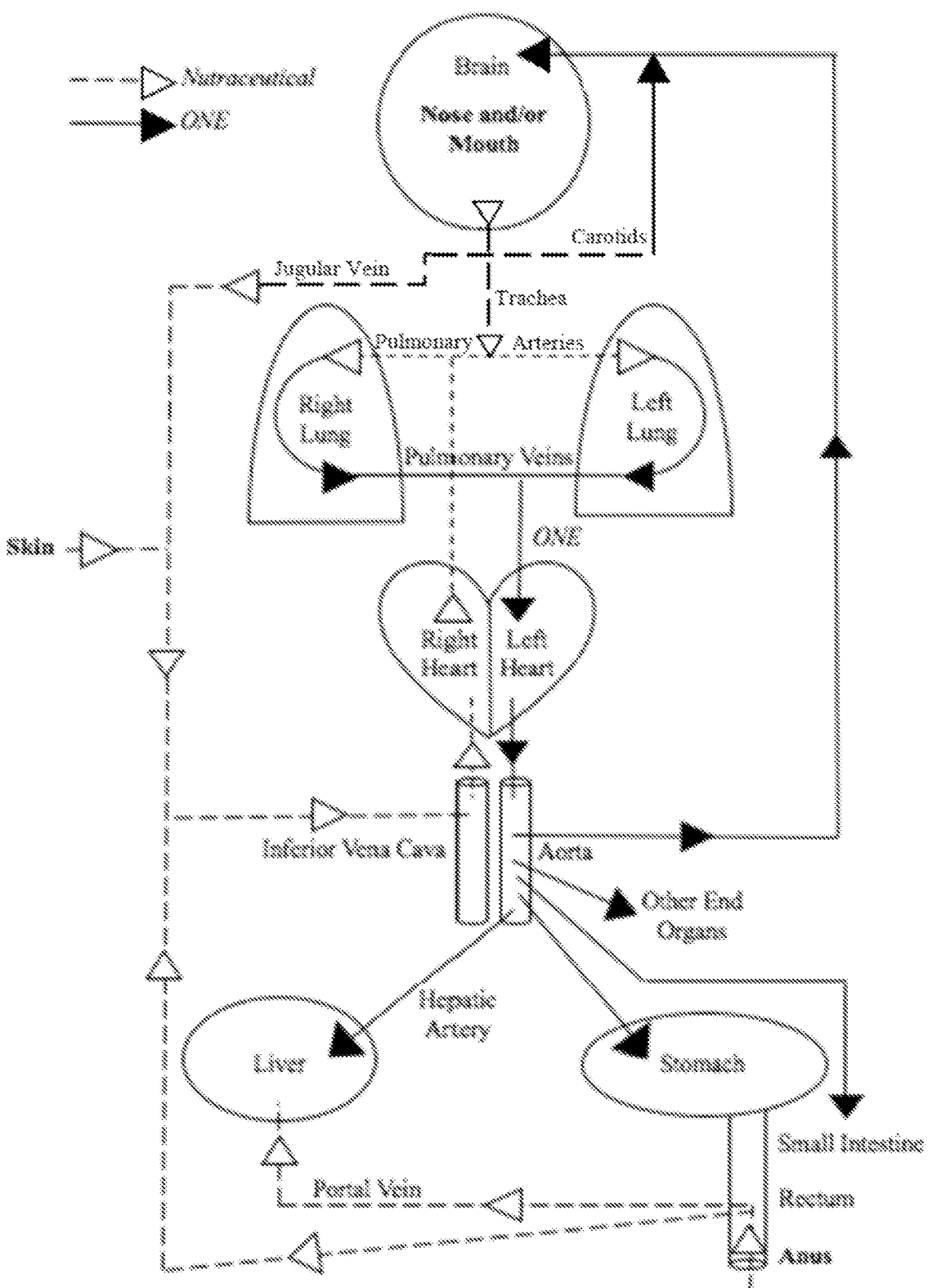
FIG. 2 illustrates the distribution of an exemplary nutraceutical composition of the invention (Nutraceutical) via direct absorption into the bloodstream from the vasculature supporting the nose, mouth, respiratory pathway, skin, and/or the lower gastrointestinal tract, including the rectum and anus.

In certain exemplary embodiments of the invention, the therapeutic effect works by direct absorption into the general blood circulation of nutraceuticals. In these embodiments the nutraceutical composition may be administered to an individual via the buccal mucosa, sublingual mucosa, nasal mucosa, respiratory mucosa, rectal and/or anal mucosa. These administration routes are illustrated in FIG. 2. The suitable dosage forms for such administration routes may include a gel, strip, film, chewable, tablet, fast absorbing tablet, quick dissolving tablet, powder, spray including but not limited to atomizer, vaporizer, aerosol or pump sprays, solution, droplet or auto-injector, suppository, and/or enema.

ONE is distributed directly to the brain via arterial branches of the internal and external carotid arteries passing approximate to and through the mouth. This is not described in prior art. The advantage of ONE travelling directly to the brain impacts veisalgia morbidity expediently.

Additionally, once absorbed into the venous vasculature, the veins drain and transport nutraceutical-enriched blood to the vena cavas and then to the right heart. The right heart sends nutraceutical-enriched blood to the lungs via the pulmonary arteries. In the lungs nutraceutical-enriched blood is oxygenated (ONE). ONE is carried by the pulmonary veins to the left heart. ONE is transported from the left heart via the aorta to end organs through their arterial branches. Veisalgia is ameliorated as end organs directly utilize ONE to neutralize OATI.

This novel method for nutraceutical delivery circumvents the nutraceuticals competing for absorption postprandial. The nutraceutical composition may be delivered 30 minutes prior to alcohol consumption, during alcohol consumption, after alcohol consumption, or the day following alcohol consumption and regardless of food intake.

This novel method for nutraceutical delivery circumvents nausea and vomiting, common symptoms of veisalgia, and the nutraceutical composition may be delivered 30 minutes prior to alcohol consumption, during alcohol consumption, after alcohol consumption, or the day following alcohol consumption and regardless of food intake.

In those exemplary embodiments of the invention that work by direct absorption into the general blood circulation of nutraceuticals via the buccal mucosa or sublingual mucosa, the nutraceutical composition may be administered by a sublingual or buccal gel, strip, film, chewable, tablet, fast absorbing tablet, quick dissolving tablet, powder, spray, solution, droplet, or an auto-injector. The extensive vascular plexus of the mouth including but not limited to the floor, beneath the tongue, and buccal areas flows through to the jugular vein as well as arterial branches of the internal and external carotid arteries passing approximate to and through the mouth. The invention's novel deliveries of nutraceuticals by sublingual or buccal gel, strip, film, chewable, tablet, fast absorbing tablet, quick dissolving tablet, powder, atomizer, vaporizer, spray, droplet, or auto-injector allow the blood to become directly enriched with nutraceuticals for neutralization of alcohol and its toxins, bypassing the gastrointestinal digestive route. Micronization and nanonization of the nutraceuticals potentiate and improve absorption. The illustrated nutraceutical distribution via direct absorption into the bloodstream from the mouth is included in FIG. 2.

In those exemplary embodiments of the invention that work by direct absorption into the general blood circulation of nutraceuticals via the nasal mucosa, the nutraceutical composition may be administered by nasal spray including but not limited to aerosol or pump spray, solution, powder, gel, strip, film, droplet, or auto-injector. The large surface area of richly vascularized nasal mucosa is drained via the jugular vein. The invention's novel deliveries of nutraceuticals by nasal spray, atomizer, vaporizer, solution, powder, gel, strip, film, droplet or auto-injector allow the blood to become directly enriched with nutraceuticals for neutralization of alcohol and its toxins, bypassing the gastrointestinal digestive route. Micronization and nanonization of the nutraceuticals potentiate and improve absorption. The illustrated nutraceutical distribution via direct absorption into the bloodstream from the nose is included in FIG. 2.

In those exemplary embodiments of the invention that work by direct absorption into the general blood circulation of nutraceuticals via the upper respiratory system, including the nose, pharynx and mouth, the nutraceutical composition may be administered by inhalation including but limited to nasal spray including but not limited to atomizer, vaporizer, aerosol or pump spray, solution, powder, gel, strip, film, droplet, or auto-injector. The invention's novel deliveries of nutraceuticals by atomizer, vaporizer, nasal spray, solution, powder, gel, strip, film, droplet or auto-injector allow the blood to become directly enriched with nutraceuticals for neutralization of alcohol and its toxins, bypassing the gastrointestinal digestive route. Micronization and nanonization of the nutraceuticals potentiate and improve absorption. The illustrated nutraceutical distribution via direct absorption into the bloodstream from the nose and/or mouth is included in FIG. 2.

In those exemplary embodiments of the invention that work by direct absorption into the general blood circulation of nutraceuticals via the respiratory pathway, including the mouth, pharynx, nose, trachea, bronchi, bronchioles and alveoli, the nutraceutical composition may be administered by inhalation including but limited to nasal spray including but not limited to atomizer, vaporizer, aerosol or pump spray, solution, powder, gel, strip, film, droplet, or auto-injector. The invention's novel deliveries of nutraceuticals by atomizer, vaporizer, nasal spray, solution, powder, gel, strip, film, droplet or auto-injector allow the blood to become directly enriched with nutraceuticals for neutralization of alcohol and its toxins, bypassing the gastrointestinal digestive route. Micronization and nanonization of the nutraceuticals potentiate and improve absorption. The illustrated nutraceutical distribution via direct absorption into the bloodstream from the nose and/or mouth is included in FIG. 2.

In those exemplary embodiments of the invention in which the very rich portal-caval anastomotic vascular plexus of the rectum and anal mucosa is used for delivery of nutraceuticals, the nutraceutical composition is administered by suppository, enema or auto-injector. In the rectum and anus, nutraceuticals are transported by the rectal venous plexus to the inferior vena cava and also to the portal vein via the portal-caval anastomosis, thereby both utilizing and bypassing first pass metabolism of the gastrointestinal digestive route. The illustrated nutraceutical distribution via direct absorption into the bloodstream from the rectum and/or anus is included in FIG. 2.

In other exemplary embodiments of the invention, the method involves administration via dermal absorption, thereby utilizing the skin for delivery of nutraceuticals. In these embodiments, the nutraceutical composition may be, for example, in the form of cream, lotion, solution, ointment, gel, patch, strip, film, spray, droplet or delivered by auto-injector, bypassing the gastrointestinal digestive route. In order to potentiate absorption through the skin, nutraceuticals may be micronized or nanonized to potentiate transport. The illustrated nutraceutical distribution via direct absorption into the bloodstream from the skin is included in FIG. 2.

Figure 3:
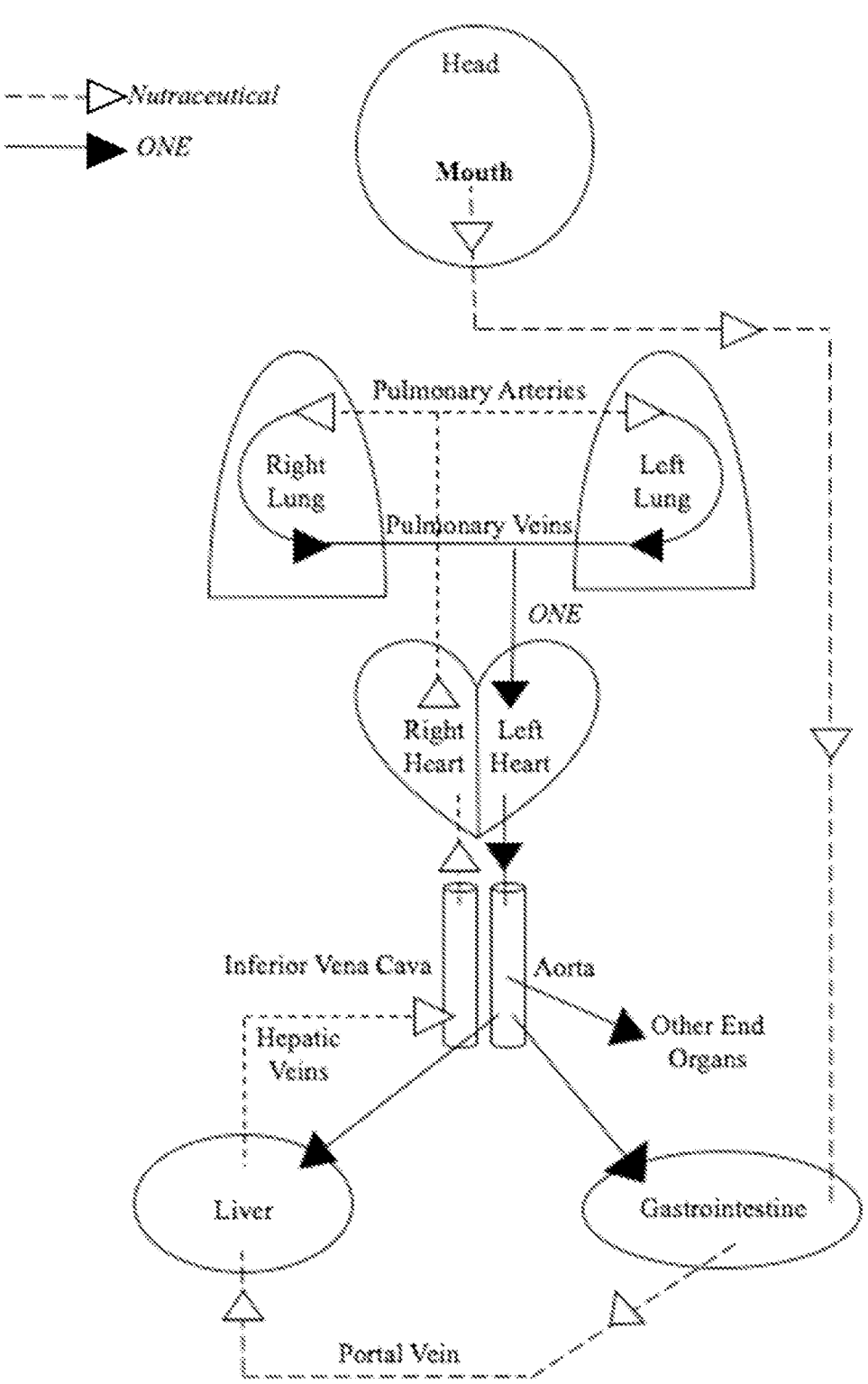
FIG. 3 illustrates distribution of an exemplary nutraceutical composition (Nutraceutical) via ingestion and distribution of oxygenated nutraceutical-enriched blood (ONE) oxygenated in the lungs and circulated through the arterial system to the liver, brain and other end organs.

In further exemplary embodiments of the invention, the method involves administering the nutraceuticals via the gastrointestinal tract through ingestion of the nutraceutical composition. In these embodiments, the nutraceutical composition may be, for example, in a dosage form such as a powder, chewables, tablets, fast absorbing tablets, quick dissolving tablets, capsules, caplets, gel caps, liquids, sprays, droplets or by autoinjectors. Nutraceutical distribution via digestion is illustrated in FIG. 3. In order to potentiate absorption through the gastrointestine, nutraceuticals are micronized or nanonized to potentiate intercellular and intracellular transport. Because nausea and vomiting have an adverse impact on nutraceutical absorption, the quicker and more efficient the delivery method, the more effective the outcome. Micronization and nanonization of the nutraceuticals potentiate and improve absorption via the gastrointestinal tract.

Under ideal circumstances, our bodies reduce alcohol to acetaldehyde and onward to harmless substances utilizing molecules including but not limited to ADH, ALDH, NAD+, lipid peroxidase, Superoxide dismutase, catalase and glutathione peroxidase in the liver; and catalase, MEOS, NADP+ and cytochrome P450 in the brain and elsewhere in the body.

In some exemplary embodiments of the invention, the nutraceutical composition provides detoxification, antioxidant activity, and cellular support, with the nutraceuticals Vitamins C & E, L-Glutathione, silymarin, and zinc. Further molecular support, specifically ADH and glutathione support, and liver and brain protection may be provided with the addition of Vitamin B9, Vitamin B12, taurine, and dihydromyricetin. An exemplary therapeutically effective amount of the nutraceutical composition may deliver to the individual for example, 125 mg to 350 mg of Vitamin C, 1.8 mg to 10 mg of Vitamin E, 1 mg to 100 mg of L-Glutathione, 165 g to 205 mg of silymarin, and 0.4 mg to 3.5 mg of zinc, or with the further addition of 540 µg to 660 µg of Vitamin B9, 15 µg to 250 µg of Vitamin B12, 90 mg to 110 mg of taurine, and 36 mg to 50 mg of dihydromyricetin. The nutraceutical composition may be administered, for example, by a cream, lotion, solution, ointment, patch, gel, strip, film, powder, chewable, tablet, fast absorbing tablet, quick dissolving tablet, capsule, caplet, gel cap, liquid, spray, droplet, auto-injector, atomizer, bong, cigarette, vape, vaporizer, volcano, suppository, or enema, depending on the desired delivery route. Suitable pharmaceutically acceptable carrier(s) and/or excipient(s) may be included to provide the composition in the desired delivery form. In these exemplary embodiments, a therapeutically effective amount may be delivered to an individual 30 minutes prior to consuming one or more alcohol beverages, during alcohol consumption, after alcohol consumption, or the day following alcohol consumption.

As alcohol is processed, some of the metabolic changes that occur include oxygen deficit, hypoxia to cell structures, production of reactive oxygen containing molecules called free radicals or reactive oxygen species ROS that damage cells and cause inflammation. In some exemplary embodiments of the invention, the endocannabinoid system known to repair damaged cells and reduce inflammation is supported and supplemented with the above listed nutraceuticals including but not limited to CBD. In particular, CBD provides molecular support for metabolism, anti-inflammation and to scavenge and process toxins. An exemplary therapeutically effective amount of the nutraceutical composition may deliver to the individual, for example, 0.01 mg to 100 mg of CBD.

In some exemplary embodiments of the invention, toxins are neutralized with molecules having flavonoid, antioxidant and anti-inflammatory properties including Vitamins B2, B6, B9, B12, dihydromyricetin, taurine, silymarin, Vitamins C & E, L-Glutathione and zinc. In these embodiments, a therapeutically effective amount of the nutraceutical composition may deliver to the individual 8 mg to 20 mg of Vitamin B2, 16 mg to 20 mg of Vitamin B6, 540 µg to 660 µg of Vitamin B9, 15 µg to 250 µg of Vitamin B12, 36 mg to 50 mg of dihydromyricetin, 90 mg to 110 mg of taurine, 165 mg to 205 mg of silymarin, 125 mg to 350 mg of Vitamin C, 1.8 mg to 10 mg of Vitamin E, 1 mg to 100 mg of L-Glutathione, and 0.4 mg to 3.5 mg of zinc. In particular, the therapeutically effective amount of the nutraceutical composition delivers no less than 183.76 mg of silymarin, no less than 140 mg of Vitamin C, no less than 2.01 mg of Vitamin E, no less than 10 mg of L-Glutathione, and no less than 0.48 mg of zinc. The nutraceutical composition may be administered, for example, by a cream, lotion, solution, ointment, patch, gel, strip, film, powder, chewable, tablet, fast absorbing tablet, quick dissolving tablet, capsule, caplet, gel cap, liquid, spray, droplet, auto-injector, atomizer, bong, cigarette, vape, vaporizer, volcano, suppository, or enema, depending on the desired delivery route. Suitable pharmaceutically acceptable carrier(s) and/or excipient(s) may be included to provide the composition in the desired delivery form. In these exemplary embodiments, a therapeutically effective amount may be delivered 30 minutes prior to consuming one or more alcohol beverages, during alcohol consumption, after alcohol consumption, or the day following alcohol consumption.

Alcohol metabolism alters the ratio of NAD+ to NADH and reduces availability of glucose causing reduced gluconeogenesis causing hypoglycemia. These changes reduce cellular energy production and impair neutralization of alcohol and toxins.

In some exemplary embodiments of the invention, replenishment of glucose and energy may be assisted by the nutraceuticals Vitamin B1, Vitamin B2, zinc, potassium, Vitamin B3, Vitamin B5, Vitamin B6, and Vitamin B12. In these embodiments, the therapeutically effective amount of the composition may deliver, 0.40 mg to 20 mg Vitamin B1, 8 mg to 20 mg of Vitamin B2, 0.4 mg to 3.5 mg of zinc, 12 mg to 55 mg of potassium, 9 mg to 30 mg of Vitamin B3, 10 mg to 22 mg of Vitamin B5, 16 mg to 20 mg of Vitamin B6, and 15 µg to 250 µg of Vitamin B12. In particular, the therapeutically effective amount of the nutraceutical composition delivers no less than 0.45 mg Vitamin B1, no less than 9.5 mg of Vitamin B2, no less than 0.48 mg of zinc, no less than 19 mg of potassium, no less than 10.8 mg of Vitamin B3, no less than 12 mg of Vitamin B5, and no less than 18 mg of Vitamin B6. The nutraceutical composition may be administered, for example, by a cream, lotion, solution, ointment, patch, gel, strip, film, powder, chewable, tablet, fast absorbing tablet, quick dissolving tablet, capsule, caplet, gel cap, liquid, spray, droplet, auto-injector, atomizer, bong, cigarette, vape, vaporizer, volcano, suppository, or enema, depending on the desired delivery route. Suitable pharmaceutically acceptable carrier(s) and/or excipient(s) may be included to provide the composition in the desired delivery form. In these exemplary embodiments, a therapeutically effective amount may be delivered 30 minutes prior to consuming one or more alcohol beverages, during alcohol consumption, after alcohol consumption, or the day following alcohol consumption.

In some exemplary embodiments of the invention, the nutraceutical composition may provide ADH and glutathione support, neutralize toxins and/or support replenishment of glucose and energy. These exemplary embodiments may use any combination of the nutraceuticals previously described.

Figure 4:
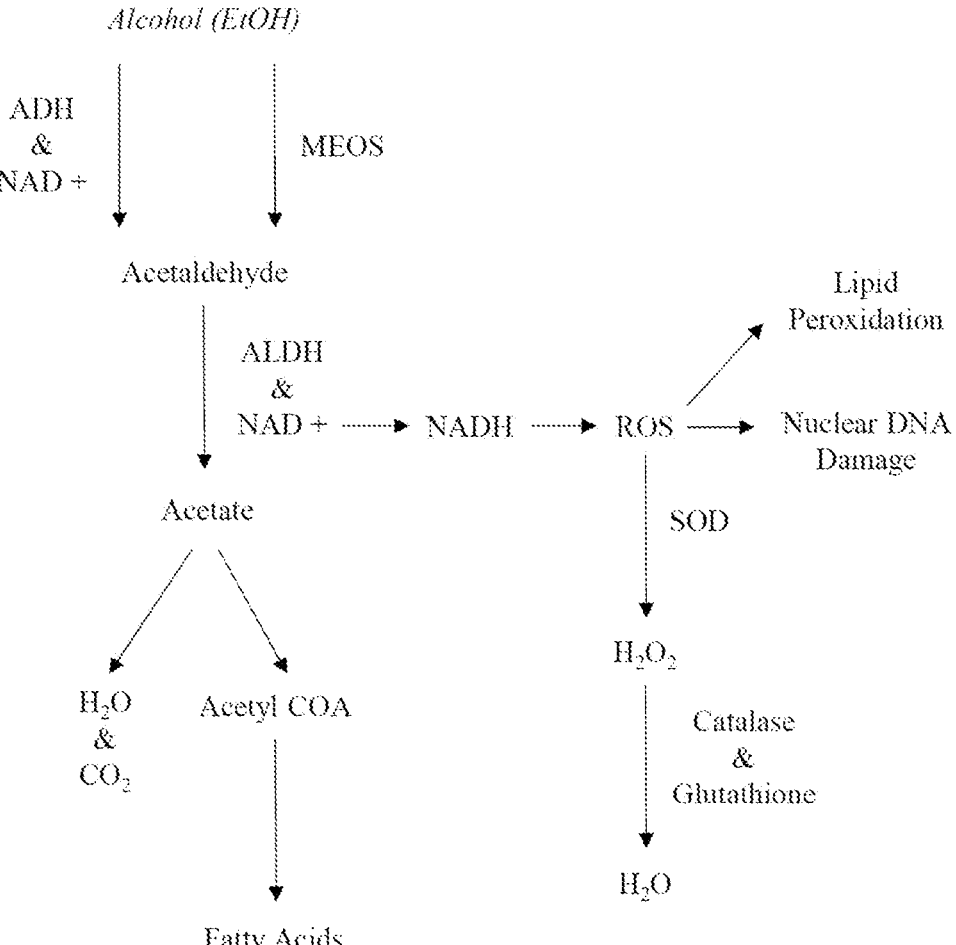
FIG. 4 illustrates an overview of alcohol metabolism and neutralization.

The invention also supports molecules used by gastrointestinal mucosal cells containing ADH and MEOS and addresses acetaldehyde produced by gastrointestinal bacteria. Part of first pass metabolism starts in the gastrointestine and continues in the liver, to a lesser extent alcohol is metabolized to acetaldehyde further in the gastrointestinal tract. Non-liver tissues that lack ADH and ALDH metabolize alcohol using other molecules as described above including Cytochrome P450 and catalase systems, as for example in the brain. The invention provides nutraceuticals to support molecules for the metabolism and neutralization of alcohol and toxins in end organs, an overview of which is shown in FIG. 4.

In some exemplary embodiments, mitigation and prevention of veisalgia are affected by the particular nutraceutical combination. For example, a nutraceutical composition may provide mitigation of veisalgia with Vitamin C, Vitamin B1, Vitamin B2, Vitamin B3, Vitamin B5, Vitamin B6, Vitamin B9, Vitamin B12, and zinc. These nutraceuticals provide molecular support for basic metabolism, building blocks to replenish spent enzymes and coenzymes, support to liver detoxification processes, support to cellular energy production, anti-inflammatory and antioxidant activity, and the therapeutically effective amounts providing mitigation of veisalgia are 125 mg to 350 mg of Vitamin C, 0.40 mg to 20 mg Vitamin B1, 8 mg to 20 mg of Vitamin B2, 9 mg to 30 mg of Vitamin B3, 10 mg to 22 mg of Vitamin B5, 16 mg to 20 mg of Vitamin B6, 540 µg to 660 µg of Vitamin B9, 15 µg to 250 µg of Vitamin B12, and 0.4 mg to 3.5 mg of zinc. The nutraceutical composition may be administered, for example, by a cream, lotion, solution, ointment, patch, gel, strip, film, powder, chewable, tablet, fast absorbing tablet, quick dissolving tablet, capsule, caplet, gelcap, atomizer, vaporizer liquid, spray, droplet, auto-injector, suppository, or enema, depending on the desired delivery route. Suitable pharmaceutically acceptable carrier(s) and/or excipient(s) may be included to provide the composition in the desired delivery form. In these exemplary embodiments, a therapeutically effective amount may be delivered 30 minutes prior to consuming one or more alcohol beverages, during alcohol consumption, after alcohol consumption, or the day following alcohol consumption.

For further improvement of the mitigation effect of the composition with Vitamin C, Vitamin B1, Vitamin B2, Vitamin B3, Vitamin B5, Vitamin B6, Vitamin B9, Vitamin B12, and zinc, silymarin can be added to the nutraceutical composition to provide molecular support reducing oxidative stress for liver and brain cell repair, protection and prevention of cell injury and cell protection. A therapeutically effective amount of silymarin is 165 mg to 205 mg.

L-Glutathione and dihydromyricetin may also be added to further enhance the mitigation effect of Vitamin C, Vitamin B1, Vitamin B2, Vitamin B3, Vitamin B5, Vitamin B6, Vitamin B9, Vitamin B12, zinc, and silymarin. L-Glutathione and dihydromyricetin provide additional molecular support for metabolism while boosting immunity to further scavenge toxins. The therapeutically effective amounts are 1 mg to 100 mg of L-Glutathione and 36 mg to 50 mg of dihydromyricetin.

Prevention of veisalgia may be achieved by the further addition of potassium, taurine, and Vitamin E to the combination of Vitamin C, Vitamin B1, Vitamin B2, Vitamin B3, Vitamin B5, Vitamin B6, Vitamin B9, Vitamin B12, zinc, silymarin. L-Glutathione, and dihydromyricetin. Potassium, taurine, and Vitamin E provide molecular support for basic metabolic functions, while protecting cells against free radical damage throughout the body including the brain while supporting liver function. The therapeutically effective amounts of these nutraceuticals are 12 mg to 55 mg of potassium, 90 mg to 110 mg of taurine, and 1.8 mg to 10 mg of Vitamin E.

In the forgoing exemplary embodiments, because micronization and nanonization potentiate and improve absorption, a lower therapeutically effective amount is required. For example, for nanonized nutraceuticals, the range is from 0.01 to 500 nm. For micronization, therapeutically effective amounts may be as low as 0.04 mg to 0.40 mg of Vitamin B1, 0.8 mg to 8 mg of Vitamin B2, 0.9 mg to 9 mg of Vitamin B3, 1 mg to 10 mg of Vitamin B5, 1.6 mg to 16 mg of Vitamin B6, 54 μg to 540 μg of Vitamin B9, 1.5 μg to 15 μg of Vitamin B12, 1.2 mg to 12 mg of potassium, 12.5 mg to 150 mg of Vitamin C, 0.18 mg to 1.8 mg of Vitamin E, 0.04 mg to 0.4 mg of zinc, 1 mg to 100 mg of L-Glutathione, 3.6 mg to 36 mg of dihydromyricetin, 16.5 mg to 165 mg of silymarin, and 9 mg to 90 mg of taurine.

The above described exemplary compositions and exemplary therapeutically effective amounts are suitable for achieving prevention and mitigation of veisalgia.

The efficacy of the invention is demonstrated by the following example:

Fast dissolving, quick absorbing chewable tablets were prepared based on a nutraceutical composition of an exemplary embodiment of the invention, which involves delivery to buccal and sublingual mucosa for direct absorption of the nutraceutical into the bloodstream. Each dose was comprised of two (2) tablets, each having a weight of approximately 2540 mg. The dose delivered 560.6068 mg of active ingredients: 140 mg of Vitamin C, 2.01 mg of Vitamin E, 0.45 mg of Vitamin B1, 9.5 mg of Vitamin B2, 0.48 mg of zinc, 19 mg of potassium, 10.8 mg of Vitamin B3, 12 mg of Vitamin B5, 18 mg of Vitamin B6, 600 μg of Vitamin B9, 16.8 μg of Vitamin B12, 183.75 mg of silymarin, 100 mg of taurine, 40 mg of dihydromyricetin, and 24 mg of N-acetyl cysteine. The dose also included 4519.392 mg of inactive ingredients: sorbitol, microcrystalline cellulose, crospovidone, stearic acid, magnesium stearate, citric acid, silicon dioxide, natural flavors and sucralose.

Thirty-five participants were instructed to consume alcoholic beverages of their choosing. After consuming the alcohol, and before going to sleep, the participants were instructed to chew 2 tablets and to complete a survey no sooner than the following day.

In the survey, participants were asked to report: (a) number of alcoholic beverages they consumed in three categories: Beer, Wine, and Liquor, (b) their certainty in the accounting of alcoholic intake, (c) their rating on a scale of 1-5 how they would expect to feel given how much alcohol they consumed, how much water they consumed, and how much food they consumed, without any supplements, and (d) their rating on a scale of 1-5 how they actually did feel. The 1-5 scale given to participants included the following descriptors:

1=today is cancelled
2=feelin' pretty rough
3=hungover but functioning
4=feelin' pretty good
5=today is excellent Of the total 35 participants, 31 participants (88.5%) experienced mitigation and/or prevention after consuming an average of 7.7 alcoholic beverages. Of these 31 participants, 18 participants (or 51.4% of the total 35 participants) experienced prevention, after consuming an average of 6.6 alcoholic beverages, and 13 participants (or 37.1% of the total 35 participants) experienced mitigation, after consuming an average of 9.3 alcoholic beverages. Only 4 participants (or 11.4% of the total 35 participants) experienced no improvement; these participants had an average of 5.8 alcoholic beverages.

The results of the survey are summarized in Tables 2 and 3 below.

TABLE 2

| Results of all 35 participants. | | | |
|---|---|---|---|
| Average number of alcoholic beverages consumed | Average "expected" feeling rating | Average "actual" feeling rating | Average improved feeling |
| 7.5 | 2.3 | 4.4 | 2.1 times better than expected. |

TABLE 3

| Prevention Results in 18 Participants- Participants who expected to feel a 4 or worse, but actually felt a 5. | | | |
|---|---|---|---|
| Average number of alcoholic beverages consumed | Average "expected" feeling rating | Average "actual" feeling rating | Average improved feeling |
| 6.6 | 2.7 | 5.0 | 2.3 times better than expected. |

Table 2 proves that the method and nutraceutical composition according to the invention effectively, on average, ameliorates veisalgia.

Table 3 proves that the method and nutraceutical composition according to the invention is a prophylactic therapy and completely prevented veisalgia in more than 50% of the participants.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments may be made by those skilled in the art without departing from the scope of the invention as defined by the following claims.

What is claimed is:

1. A nutraceutical composition comprising 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, and 0.04 mg to 3.5 mg of zinc, wherein said composition provides therapeutically effective amounts of Vitamin C, Vitamin B1, Vitamin B2, Vitamin B3, Vitamin B5, Vitamin B6, Vitamin B9, Vitamin B12, and zinc, that mitigate veisalgia by providing molecular support for basic metabolism, building blocks to replenish spent enzymes and coenzymes, support to liver detoxification processes, support to cellular energy production, anti-inflammatory and antioxidant activity, and the composition further comprises a therapeutically effective amount of silymarin and L-Glutathione, wherein the therapeutically effective amount of silymarin further provides molecular support reducing oxidative stress for liver and brain cell repair, protection and prevention of cell injury and cell protection, and wherein therapeutically effective amount of L-Glutathione further provides molecular support for metabolism while boosting immunity to further scavenge toxins.

2. The nutraceutical composition according to claim 1, wherein the composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 16.5 mg to 205 mg of silymarin, and 1 mg to 100 mg L-Glutathione.

3. The nutraceutical composition according to claim 1, further comprising a therapeutically effective amount of dihydromyricetin, wherein the therapeutically effective amount of dihydromyricetin further provides molecular support for metabolism while boosting immunity to further scavenge toxins.

4. The nutraceutical composition according to claim 3, wherein composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 16.5 mg to 205 mg of silymarin, 1 mg to 100 mg of L-Glutathione, and 3.6 mg to 50 mg of dihydromyricetin.

5. The nutraceutical composition according to claim 3, further comprising a therapeutically effective amount of potassium, taurine, and Vitamin E, wherein the therapeutically effective amount of potassium, taurine, and Vitamin E further provides molecular support for basic metabolic functions, while protecting cells against free radical damage throughout the body including the brain while supporting liver function.

6. The nutraceutical composition according to claim 5, wherein composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 16.5 mg to 205 mg of silymarin, 1 mg to 100 mg of L-Glutathione, 3.6 mg to 50 mg of dihydromyricetin, 1.2 mg to 55 mg of potassium, 9 mg to 110 mg of taurine, and 0.18 mg to 10 mg of Vitamin E.

7. The nutraceutical composition according to claim 1, further comprising a therapeutically effective amount of potassium, taurine, and Vitamin E, wherein the therapeutically effective amount of potassium, taurine, and Vitamin E further provides molecular support for basic metabolic functions, while protecting cells against free radical damage throughout the body including the brain while supporting liver function.

8. The nutraceutical composition according to claim 7, wherein composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 16.5 mg to 205 mg of silymarin, 1 mg to 100 mg L-Glutathione, 1.2 mg to 55 mg of potassium, 9 mg to 110 mg of taurine, and 0.18 mg to 10 mg of Vitamin E.

9. The nutraceutical composition according to claim 1, further comprising a therapeutically effective amount of cannabidiol (CBD), wherein the therapeutically effective amount of CBD further provides molecular support for metabolism, anti-inflammation and to scavenge and process toxins.

10. The nutraceutical composition according to claim 9, wherein the composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 1 mg to 100 mg L-Glutathione, and 0.01 mg to 100 mg of CBD.

11. The nutraceutical composition according to claim 9, further comprising a therapeutically effective amount of dihydromyricetin, potassium, taurine, and Vitamin E, wherein these therapeutically effective composites further boost immunity, protect cells against free radical damage throughout the body including the brain and support liver function.

12. The nutraceutical composition according to claim 11, wherein composition comprises 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 0.01 mg to 100 mg of CBD, 16.5 mg to 205 mg of silymarin, 1 mg to 100 mg of L-Glutathione, 3.6 mg to 50 mg of dihydromyricetin, 1.2 mg to 55 mg of potassium, 9 mg to 110 mg of taurine, and 0.18 mg to 10 mg of Vitamin E.

13. A nutraceutical composition comprising 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 µg to 660 µg of Vitamin B9, 1.5 µg to 250 µg of Vitamin B12, 0.04 mg to 3.5 mg of zinc, 1 mg to 100 mg of L-Glutathione, and 0.01 mg to 100 mg of CBD, a. wherein said composition provides a therapeutically effective amounts of Vitamin C, Vitamin B1, Vitamin B2, Vitamin B3, Vitamin B5, Vitamin B6, Vitamin B9, Vitamin B12, and zinc that mitigate veisalgia by providing molecular support for basic metabolism, building blocks to replenish spent enzymes and coenzymes, support to liver detoxification processes, support to cellular energy production, anti-inflammatory and antioxidant activity, b. wherein said composition provides a therapeutically effective amount of L-Glutathione further provides molecular support for metabolism while boosting immunity to further scavenge toxins and c. wherein said composition provides a therapeutically effective amount of CBD that further provides molecular support for metabolism, anti-inflammation and to scavenge and process toxins.

14. A nutraceutical composition comprising 12.5 mg to 350 mg of Vitamin C, 0.04 mg to 20 mg Vitamin B1, 0.8 mg to 20 mg of Vitamin B2, 0.9 mg to 30 mg of Vitamin B3, 1 mg to 22 mg of Vitamin B5, 1.6 mg to 20 mg of Vitamin B6, 54 μg to 660 μg of Vitamin B9, 1.5 μg to 250 μg of Vitamin B12, 0.04 mg to 3.5 mg of zinc, and 1 mg to 100 mg of L-Glutathione, wherein said composition provides therapeutically effective amounts of Vitamin C, Vitamin B1, Vitamin B2, Vitamin B3, Vitamin B5, Vitamin B6, Vitamin B9, Vitamin B12, and zinc, that mitigate veisalgia by providing molecular support for basic metabolism, building blocks to replenish spent enzymes and coenzymes, support to liver detoxification processes, support to cellular energy production, anti-inflammatory and antioxidant activity, wherein said composition provides a therapeutically effective amount of L-Glutathione further provides molecular support for metabolism while boosting immunity to further scavenge toxins the composition further comprising a therapeutically effective amount of cannabidiol (CBD), wherein the therapeutically effective amount of CBD further provides molecular support for metabolism, anti-inflammation and to scavenge and process toxins.

* * * * *